United States Patent [19]

Kulkarni

[11] Patent Number: 5,191,149

[45] Date of Patent: Mar. 2, 1993

[54] METHOD OF REFINING LIQUIFIED PETROLEUM GASES INTO AEROSOL PROPELLANTS

[76] Inventor: Rajendra D. Kulkarni, 1127 Juniper Canyon La., Houston, Tex. 77062

[21] Appl. No.: 729,285

[22] Filed: Jul. 12, 1991

[51] Int. Cl.⁵ .......................... C07C 7/00; C07C 7/12; C07C 7/17; C01B 17/16
[52] U.S. Cl. .................................. 585/802; 585/820; 585/836; 585/841; 585/853; 585/854; 585/856; 585/868; 423/221; 423/245.1
[58] Field of Search ............... 585/802, 836, 841, 853, 585/854, 856, 868, 820; 423/221, 245.1

[56] References Cited

U.S. PATENT DOCUMENTS

| | | | |
|---|---|---|---|
| 3,281,484 | 10/1966 | Van Pool | 585/853 |
| 4,108,916 | 8/1978 | Mears | 260/676 R |
| 4,162,272 | 7/1979 | Vautrain | 585/802 |
| 4,351,980 | 9/1982 | Reusser et al. | 585/820 |
| 4,425,226 | 1/1984 | Reusser et al. | 208/307 |
| 4,491,563 | 1/1985 | Reusser et al. | 422/5 |

*Primary Examiner*—Anthony McFarlane
*Assistant Examiner*—Nhat Phan
*Attorney, Agent, or Firm*—Fulbright & Jaworski

[57] ABSTRACT

A method for refining liquified petroleum gases so that gases can be treated to reduce odor, olefins, moisture and wherein side reactions are minimized to produce stable aerosol by multistage liquid-liquid extraction of the aerosol using electrolyte solutions at controlled pH, chemically treating, drying and finishing by using molecular sieves and metal sulfides.

7 Claims, 3 Drawing Sheets

SYMBOLS

GATE VALVE

CHECK VALVE

CONTROL VALVE

RELIEF VALVE

PROCESS LINE

ELECTRICAL LINE

PNEUMATIC LINE

LOCALLY WTD. INSTRUMENT

PANEL WTD. INSTRUMENT

SAGE GLASS

BACKPRESSURE REGULATING SELF CONTAINED C.V.

PRESSURE REDUCING REGULATOR SELF CONTAINED C.V.

INPUT TO COMPUTER

ROTARY PUMP

METHOD OF REFINING LIQUIFIED PETROLEUM GASES INTO AEROSOL PROPELLANTS

BACKGROUND OF THE INVENTION

Aerosol is a form of packing in which a gas under pressure, or a liquified gas which has a pressure greater than atmospheric pressure at ordinary temperatures, is used to spray a liquid. The result of spraying is to produce a mist of small liquid droplets in air. Numerous products such as paints, air fresheners, deodorizers, insecticides, waxes, cleaners, personal care products—shaving creams, deodorants, etc. are dispensed with aerosols. A typical aerosol package is a sealed unit to avoid leakage. The vapor phase consists primarily of the propellant, whereas the liquid phase is propellant dissolved in active ingredients. The contents of an aerosol contain surface active agents, stabilizers and solvents. Aerosols usually operate at pressures between 30-50 psig and may contain as much as 90% propellant.

Chlorofluorocarbons and liquified petroleum gases are two types of chemicals popular for use as aerosol propellants. In the refining of crude oil, the overheads product mainly contains mixed butanes, which can through distillation produce suitable "cuts" for the propellant industry. A typical LPG propellant will mainly contain isobutane and butane, with small amounts of propane.

The main source of propellants is the petroleum refineries and natural gas processing plants. Often the butanes are catalytically isomerized to produce isobutane. There are always traces of sulfur and other compounds that make the direct use of butanes impossible, without further treatment. These trace contaminants are removed by various means. U.S. Pat. No. 4,108,916 has revealed a method for eliminating unsaturated hydrocarbons by treating with concentrated sulfuric acid. U.S. Pat. Nos. 4,351,980; 4,425,226 and 4,491,563 have discussed the use of transition metals and clays for deodorizing through various means.

The technical literature attributes odor to a variety of chemical species such as unsaturates, ketones, alcohols, etc. Although the boiling points of the odor causing four carbon atom compounds are far enough apart, separation by distillation is not economically feasible, rarely required, and sometimes not possible.

Through various contamination processes, oxygen and oxygenated compounds are formed in butanes. One mechanism by which oxygen is introduced into the system is through walls of the pressure vessel used to transport butane. When empty or during inspections the walls of the pressure vessels are exposed to atmospheric oxygen. The surface is coated with rust, which gradually releases oxygen. Also during transfer operations, line filled oxygen ends up in the butane.

Oxygen in the presence of naturally occurring catalyst like, iron form a series of compounds like acetone, tertiary butyl hydroperoxide, methanol and isobutylene. Most of oxygenated products have a characteristic odor and are soluble in water.

It is this water soluble property that is used in the present invention to deodorize liquified petroleum gases.

Although there is abundance of butanes, only the preferred feedstocks meet rigid requirements of personal care products industry. And a high price is paid for odor free aerosol propellants. The present disclosure provides a process and a preferred embodiment to refine LPG gases and upgrade them.

SUMMARY

The present invention is directed towards treating liquified petroleum gases consisting of isobutanes, butanes and propanes, together forming at least 90% of the mixture. The invention contemplates extracting water soluble odorous trace compounds and in addition using controlled pH and chemicals by providing an environment to convert non-soluble odorous components to water soluble form or isomer, and then extracting the isomer with water.

An object of the present invention is the provision of a process of refining liquified petroleum gases containing isobutane, butane and propane for use as an aerosol propellant by removing odorous components including water soluble components by dissolving the water soluble components into an electrolyte solution, separating the electrolyte solution into a liquid stream and a hydrocarbon stream. Thereafter, the hydrocarbon stream is mixed with sodium thiosulfate, and then separating the mixed hydrocarbon and sodium thiosulfate into a hydrocarbon liquid phase and a thio liquid phase and therafter drying the hydrocarbon phase providing an aerosol propellant.

Yet a still further object of the present invention is wherein the liquified petroleum gases include non-water soluble odorous components wherein the non-water soluble components are converted to water soluble components and then removed.

Still a further object of the present invention is wherein the hydrocarbon phase is dried with salt and clay and thereafter dried using molecular sieves.

Yet still a further object of the present invention is wherein the feedstock is hydrogenated for converting non-water soluble components into water soluble components.

Yet still a further object of the present invention is wherein the electrolyte solution is at a controlled pH for converting non-water soluble components into water soluble components.

A still further object of the invention is wherein the odorous components are treated first with acid and then with caustic prior to mixing with sodium thiosulfate. During the treatment with the acid, the hydrocarbon stream is preferably maintained at a pH of about 4 to 6.

Other and further objects, features and advantages will be apparent from the following description of a presently preferred embodiment of the invention, given for the purpose of disclosure, and taken in conjunction with the accompanying drawings.

DESCRIPTION OF THE PREFERRED EMBODIMENT

The present invention will be described as refining liquid petroleum gases (LPG) containing isobutane, butane, and propane totalling at least 90% of the process mixture. In addition, the process will be described as having a plurality of steps and treatments, which, while desirable, are not all necessary depending upon the actual composition of the feedstock and depending on how highly refined the finished aerosol propellant product is desired. The feedstock contains various odorous components which must be removed in order to produce the desired grade of aerosol. First, the process is directed to dissolving the odorous water soluble components with water and removing them. In addition, in the event that the feedstock includes non-water soluble odorous components the process uses controlled pH and chemicals to convert the non-water soluble odorous components into water soluble form or isomers and then extracting them with water.

For example, a four carbon atom stream containing trace amounts of diethyl ether may be partially converted to ethanol by water washing this mixture in a pH controlled aqueous environment. The diethyl ether is only sparingly soluble in water, whereas, ethanol is completely soluble. Thus streams having four carbon atoms which also have a diethyl ether odor may be treated with this method. The water phase, with the extracted ethanol may be concentrated or disposed.

Figure 1A:
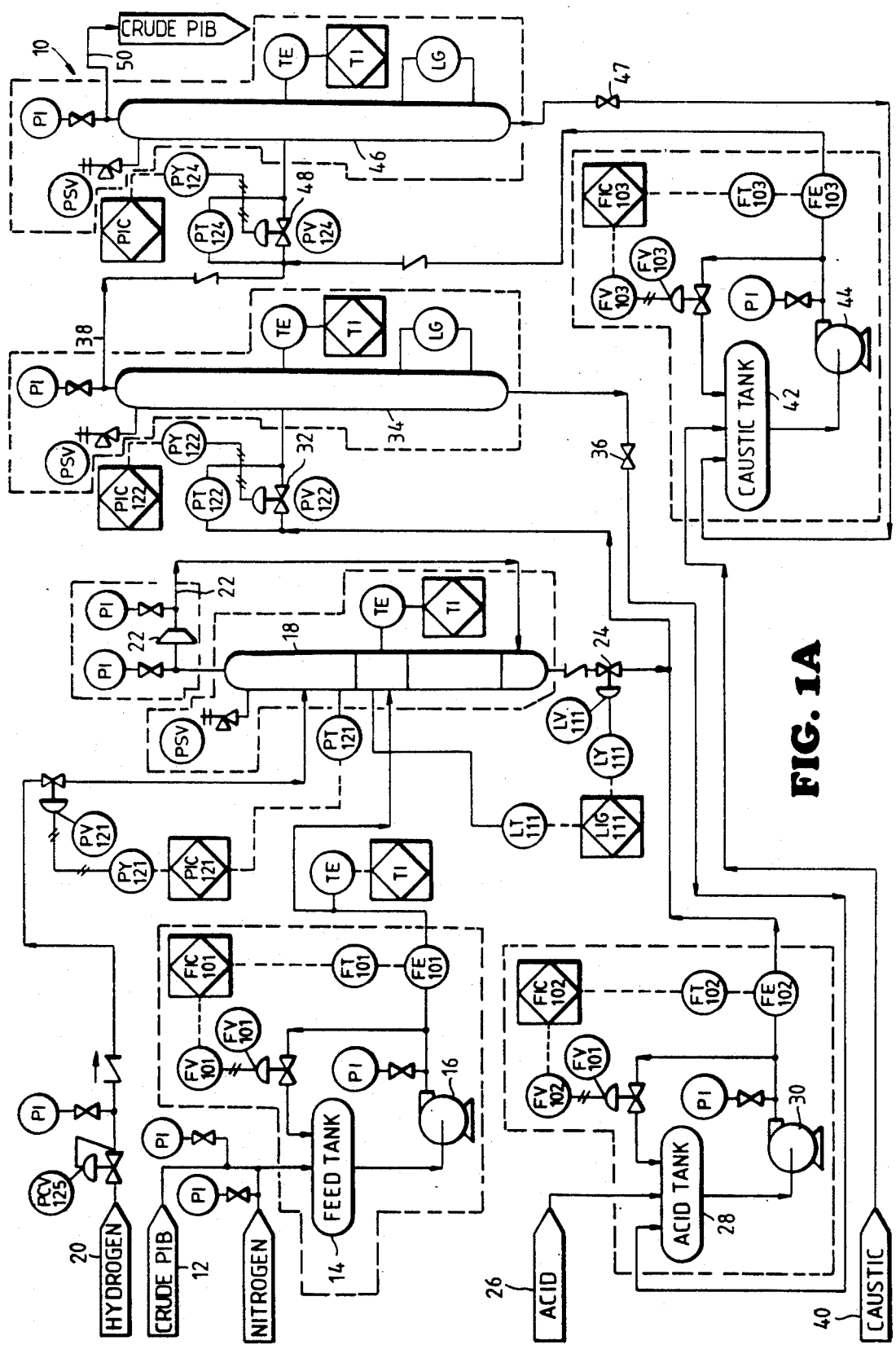
FIGS. 1A and 1B are continuations of each other and form a schematic flow diagram of the process of the present invention.
Figure 1B:
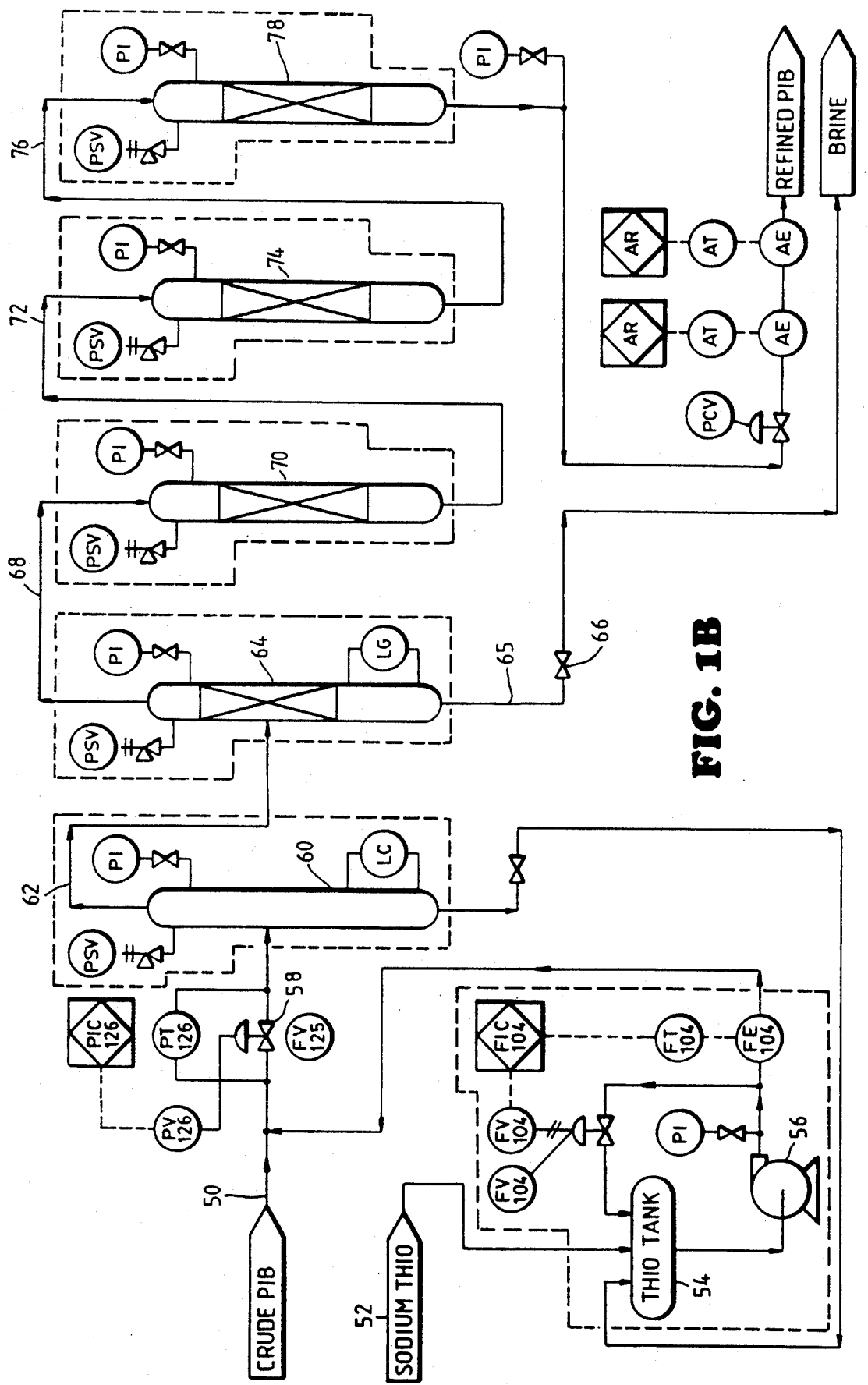
Figure 2A:
FIG. 2 is a chart explaining the symbols used in FIGS. 1A and 1B which are not described in detail in the specification as being unnecessary to the description of the present invention, but useful in providing a full enablement of the practice of the present process.
Figure 2A:
Figure 2A:
Figure 2A:
Figure 2A:
Figure 2A:
Figure 2A:
Figure 2A:
Figure 2A:
Figure 2A:
Figure 2A:
Figure 2A:
Figure 2A:
Figure 2A:

Referring now to the drawings, and particularly to FIGS. 1A and 1B, the reference numeral 10 generally indicates the process of the present invention. The LPG feedstock is received at inlet 12 and stored in feed tank 14. Feed tank 14 is normally a coded pressure vessel designed to withstand the vapor pressure of the propellant mixture. A feed pump 16 draws suction from the tank 14 and is used to flow the feed stock through the process 10. Pump 16 is equipped with a spill back system to accurately control flow of the feedstock. From the pump 16, the feedstock is transmitted to hydrogenator 18, which is a pressure vessel, which may be operated at temperatures between 90° F. and 400° F., although it is more commonly operated between 200° F. and 300° F. The hydrogenator 18 is internally filled with hydrogenation catalysts. There are a number of catalysts that can be used for hydrogenating. One type of catalysts contains about 18% transitional metal oxides, such as cobalt and molybedum, on an alumina support. Noble metal catalysts such as platinum, palladium, cobalt and nickel may be used. All of these catalysts are suitable for use, each type of course, giving its specific by-products requiring specific treatment methods. The catalysts may be spherical, extruded, or in any other shapes, such as "berl" saddles. The pressure range of the hydrogenator 18 can be as low as 60 psig to 1,000 psig, although it is more normal for the pressure to be designed between 120-250 psig. Hydrogen from the hydrogen inlet 20 is added to the hydrogenator 18 at a control rate based on the pressure of the hydrogenator 18. A liquid level is maintained in the hydrogenator 18. From the upper outlet 22 of the hydrogenator 18, a hydrogen rich gas stream is drawn, and compressed, and recirculated to the bottom of the hydrogenator by means of a gas compressor 22. The compressor 22 is used to make the mass in the hydrogenator 18 in a fluidized state, as close to the "kinetic state of gases" as possible. As the reaction proceeds, hydrogen is depleted and has to be made up with fresh hydrogen from the inlet 20. If the mass is not properly fluidized, then the basis reaction—conversion of olefins to alkanes—will not progress as designed, like in any catalytic reaction poisoning of the catalyst can also cause low conversion of olefins to alkanes. As the operating pressure of the hydrogenator 18 is reduced, the quantity of hydrogen in the off gas is also reduced, and conversely if the operating pressure is increased, the gas will be richer in hydrogen. For one design, a 50% volumetric hydrogen was selected and pressure required for the hydrogenation was about 120 psig. In the hydrogenator 18, the hydrogen converts non-water soluble odorous components to water soluble components, which may then be removed and olefins to alkanes, which are stable and less reactive. For example, the isobutylene is converted into butane. An outlet level control valve 24, which is located at the bottom of the hydrogenator 18, controls the level by adjusting the flow of liquid out of valve 24. While note shown, the stream flowing through valve 24 is cooled, such as by an air cooled heat exchanger or a closed loop water cooling tower.

An acid solution inlet 26 provides a suitable acid, such as sulfuric acid, which flows to acid tank 28, and is pumped by pump 30 directly into the hydrogenated mass leaving the control valve 24. The combined stream flows to a mixing valve 32. The purpose of the mix valve 32 is to achieve mixing of the acid and hydrogenated mass. The amount of acid injected into the process will depend upon the source and the impurities in the feedstock and the concentration of the acid. For one such design, acid in the amount of 30% of the feedstock was specified at a concentration of 1N. In this process, the upper and lower limits are 5% to 100% rate of acid flow at concentrations between 0.1 and 10N. In the absence of any previous experience, a 25% of the feedstock at 1N is the recommended dosage. It is normal to maintain a pH of about 4 to 6 using a very dilute solution of sulfuric acid. The acid settler tank 34 is a pressure vessel here shown as vertical, but it could also be operated in the horizontal position. The tank 34 is connected to a control valve 36 which is used to dump acid back into the acid tank 28. In the tank 34, the acid dissolves the acetone out in the water wash where it can be removed out through the valve 36.

The overhead stream in line 38 is lighter than the acid/water phase in the tank 34, and it is then mixed with an alkaline solution, such as a caustic solution having a caustic inlet 40, such as sodium hydroxide which is stored in tank 42 and pumped by pump 44 to a caustic settler tank 46 where it is mixed with the hydrogenated mass in line 38 and mixed in a mix valve 48 prior to entering the tank 46. The amount of alkaline solution injected into the process would depend upon the impurities and may vary from 0.1 to 75% of the feedstock on a mass basis, although it is more normal to use between 5 to 25% on a mass basis. For one such design, caustic of the amount of 22% of the feedstock was specified at a concentration of 2N. In this process, the upper and lower limits are 5% to 100% rate of feedstock flow at concentrations between 0.5 and 5N. In the absence of any previous experience, a 25% of the feed rate at 1N is the recommended treatment. The caustic wash in tank 46 is a precursor to the use of the sodium thiosulfate in the next step so as to neutralize the acid which has been inserted into the tank 34 and the water phase is separated out through a valve 47.

The stream is then treated with a sodium thiosulfate in a similar fashion. That is, the overhead stream 50 leaving the tank 46 is lighter than the caustic/water phase remaining in the tank 46, and is mixed with a thiosulfate solution (FIG. 1B). That is, a sodium thiosulfate inlet 52 is provided to store the thio in a tank 54 where it is pumped by a pump 56 to a mixing valve 58 to be mixed with the caustic washed mass leaving line 50, and the mixture is settled in a thio settler tank 60. The amount of thio solution will depend upon several factors, such as the impurities encountered, the amount of oxygen and oxygenates present in the feedstream to the valve 58. The thio solution may vary from 5 to 75% of the feedstock on a mass basis, although it is more normal to use between 10 to 25% on a mass basis. For one such design, thio of the amount of 15 times the stoichiometric was specified at a concentration of 0.5N. The overhead stream 62 is lighter than the thio/water phase in the settler 60, and now can be dried and finished. The hydrocarbon phase at 62 is then dried, using salt in a salt drier 64. The salt drier 64 is a pressure vessel filled with rock or common salt pieces. Any water in the hydrocarbon phase 62 dissolves and forms brine which is withdrawn in line 65 using valve 66. The overhead stream 68 leaving the salt drier 64 enters the top and leaves the bottom of a clay drier 70. Additional water is removed by the clay drier 70. The stream 72 then flows through a molecular sieve column 74 wherein traces of moisture and odorous compounds are removed. The stream then leaves the drier 74 and flows into the drier column 78 which includes a synthetic ion exchange resin such as amberlight 400 sold by Rohm & Haas Company and metal sulfides to remove any traces of oxygen or oxygenated compounds.

After these treatments, the liquified petroleum gas feedstock is ready for use for an aerosol propellant. It is to be noted that it is desirable that the hydrocarbon phase is dried with the salt in the drier 64, and the clay in the drier 70 prior to drying using the molecular sieves in drier 74 in order to conserve the more expensive molecular sieves 74.

The following considerations are important to the present process:

(1) The hydrogenation capacity increases with the increase in the residence time in the hydrogenation vessel and the hydrogenation temperature.
(2) Water dissolves certain odorous compounds.
(3) The pH of acid/caustic used for washing alters the chemistry of products formed during the electrolyte washes and thus limits the amount of product lost with the spend electrolyte.
(4) In a continuous commercial process, it is just as important to wash the compounds and hydrogenate as it is to dry the product.

Some steps in the process 10 may be omitted if some components of the LPG feedstock doesn't contain certain odorous compounds which are desired to be treated, or if the feedstock does not need the complete treatment.

The present invention, therefore, is well adapted to carry out the objects and attain the ends and advantages mentioned, as well as others inherent therein. While a presently preferred embodiment of the invention has been given for the purpose of disclosure, numerous changes in the details of construction, and arrangement of parts, and steps of the process, will be readily apparent to those skilled in the art, and which are encompassed within the spirit of the invention and the scope of the appended claims.

What is claimed is:

1. A process of refining liquified petroleum gases containing isobutane, butane and propane for use as an aerosol propellant by removing odorous components including water soluble components, comprising,
   contacting the liquified petroleum gases with an electrolyte solution thereby dissolving the water soluble components into said electrolyte solution,
   separating the electrolyte solution into an electrolyte liquid stream and a hydrocarbon stream,
   mixing the hydrocarbon stream with sodium thiosulfate, and
   separating the mixed hydrocarbon and sodium thiosulfate into a liquid hydrocarbon phase and a liquid sodium thiosulfate phase, and
   drying the hydrocarbon phase thereby providing an aerosol propellant.

2. The process of claim 1 wherein the liquified petroleum gases include non-water soluble odorous components wherein the non-water soluble components are converted to water soluble components prior to separating the electrolyte solution and then are removed.

3. The process of claim 1 wherein,
   the hydrocarbon phase is dried with salt and clay and thereafter dried using molecular sieves.

4. The process of claim 1 wherein the liquified petroleum gases are hydrogenated prior to contacting with the electrolyte solution for converting any olefins in the liquified petroleum gases to alkanes.

5. The process of claim 1 wherein the hydrocarbon stream is treated first with an acid and then with a caustic solution prior to mixing with sodium thiosulfate to remove the odorous components.

6. The process of claim 5 wherein during the treatment with the acid the hydrocarbon stream is maintained at a pH of about 4 to 6.

7. A process of refining liquified petroleum gas containing isobutane, butane and propane for use as an aerosol propellant by removing odorous components including water soluble and non-water soluble components comprising,
   contacting the liquified petroleum gas with an electrolyte solution thereby dissolving the water soluble components into said electrolyte solution,
   hydrogenating the solution and converting the non-water soluble components to water soluble components which are then dissolved into said electrolyte solution,
   treating the solution with an acid,
   separating the solution into an electrolyte liquid stream and a hydrocarbon liquid stream,
   thereafter treating the hydrocarbon stream with a caustic solution,
   thereafter treating the hydrocarbon stream with sodium thiosulfate,
   separating the hydrocarbon stream from the sodium thiosulfate, and
   then drying the hydrocarbon stream.

* * * * *